United States Patent [19]

Paul et al.

[11] 4,440,850

[45] Apr. 3, 1984

[54] PHOTOPOLYMERISATION PROCESS WITH TWO EXPOSURES OF A SINGLE LAYER

[75] Inventors: John G. Paul, Falkirk, Scotland; Bernard P. Stark, Great Shelford, England; Ewald Losert, Rheinfelden, Switzerland

[73] Assignee: Ciba-Geigy Corporation, Ardsley, N.Y.

[21] Appl. No.: 397,373

[22] Filed: Jul. 12, 1982

[30] Foreign Application Priority Data

Jul. 23, 1981 [GB] United Kingdom ............... 8122803

[51] Int. Cl.$^3$ .............................................. G03C 5/00
[52] U.S. Cl. ..................................... 430/325; 430/270; 430/281; 430/394; 204/159.14; 204/159.22
[58] Field of Search ............... 430/270, 281, 325, 394; 204/159.14, 159.22

[56] References Cited

U.S. PATENT DOCUMENTS

| | | | |
|---|---|---|---|
| 3,926,642 | 0/1975 | Breslow et al. | 96/115 R |
| 4,106,943 | 0/1978 | Ikeda et al. | 96/115 R |
| 4,107,174 | 0/1978 | Baumann et al. | 260/326 MS |
| 4,163,763 | 0/1979 | Tsuchiya et al. | 525/290 |
| 4,291,118 | 0/1981 | Boduch et al. | 430/313 |

FOREIGN PATENT DOCUMENTS

| | | |
|---|---|---|
| 935756 | 4/1963 | United Kingdom . |
| 1263294 | 2/1972 | United Kingdom . |
| 1407069 | 9/1975 | United Kingdom . |
| 1507774 | 4/1978 | United Kingdom . |

OTHER PUBLICATIONS

Research Disclosure, Oct. 1972, No. 10234.
Research Disclosure, Dec. 1980, No. 20012.
D. R. Arnold et al., "Photochemistry", Academic Press, 1974, p. 170.

Primary Examiner—Jack P. Brammer
Attorney, Agent, or Firm—Harry Falber

[57] ABSTRACT

A layer of a liquid composition containing a compound (A) having in the same molecule at least one (meth)acryloyl group and at least one bicyclo[2.2.1]hept-2-ene-6-yl unit is exposed to actinic radiation so that the layer solidifies due to photopolymerisation of (A) through the (meth)acryloyl group(s), remaining, however, photocrosslinkable. When desired, the solidified layer is exposed, as through a negative, to a substantially greater amount of actinic radiation, the parts so further exposed becoming more highly photocrosslinked through the bicyclo[2.2.1]hept-2-ene-6-yl unit(s) and hence insoluble. An image is produced which can be developed by means of suitable solvents. Examples of (A) include 3-(methacryloyloxy)-2-hydroxypropyl bicyclo[2.2.1]hept-2-ene-6-carboxylate and 2-(acryloyloxy)ethyl methyl-5-carboxybicyclo[2.2.1]hept-2-ene-6-carboxylate.

13 Claims, No Drawings

PHOTOPOLYMERISATION PROCESS WITH TWO EXPOSURES OF A SINGLE LAYER

BACKGROUND OF THE INVENTION

This invention relates to a photopolymerisation and photocrosslinking process, and in particular to such a process for the production of images.

Conventionally, production of an image by means of photopolymerisation is achieved by coating a support with a solution in a volatile organic solvent of a photopolymerisable substance, causing or allowing the solvent to evaporate so leaving a film of the photopolymerisable substance, irradiating the film with actinic radiation as through an image whereby the parts of the film struck by the irradiation become photopolymerised (and less soluble) while those parts shielded from the irradiation remain substantially unaffected, then dissolving away the unirradiated, unphotopolymerised parts of the film by means of a suitable solvent which does not dissolve the irradiated, photopolymerised parts. This last stage is conventionally known as "development".

It would be desirable to have a process in which a layer of a photopolymerisable substance were applied to a support and this layer were converted into a substantially solid, non-tacky state, ready for irradiation, without the use of organic solvents. Not only would, in this stage, the use be avoided of solvents which might present problems of toxicity and flammability and also cause expense in their recovery, but the production on a continuous basis of coated supports, ready for irradiation, would be facilitated.

We have found that this object can be achieved by the use of certain substances which contain in the same molecule two kinds of groups through which photopolymerisation can occur at rates which differ considerably from one another. The groups are chosen so that photopolymerisation of a layer of a liquid composition occurs rapidly to form a solid, essentially tack-free layer, which is, however, still soluble in certain solvents. When desired, parts of the layer are further subjected to a substantially greater amount of actinic radiation and photocrosslinking takes place through the other type of group in the already photopolymerised molecules of the layer, the parts of the layer which undergo photocrosslinking becoming much more resistant to solution in the solvents.

Brazilian published Patent Application No. 8008428 describes a method for forming relief images from a film of a liquid photopolymerisable material, comprising exposing the film to actinic radiation so that it solidifies by chemical hardening, then re-exposing the solidified film to further actinic radiation in the form of a pattern so that parts of the film become chemically differentiated, and then selectively removing the portions of the film not exposed to the patterned exposure of actinic radiation by washing with a solvent. The only photopolymerisable materials suggested comprise a mixture of a polyene and a polythiol.

Unpublished experiments by the Applicants have shown that numerous potentially useful compounds, containing two types of units normally capable of undergoing photopolymerisation, do not give satisfactory results in such a process, photopolymerisation in the first stage being much retarded, apparently as a consequence of the presence in the molecule of another type of photopolymerisable unit, despite the incorporation of a variety of photoinitiators and photosensitisers. In other unpublished experiments of the Applicants, mixtures of two compounds, one containing a unit normally capable of undergoing photopolymerisation and the other containing a unit normally capable of undergoing dimerisation on exposure to irradiation, gave unsatisfactory results, apparently due to inhibition of the photocrosslinking reaction.

It has been found that the desired process can be achieved by employing a compound which contains in the same molecule both one or more acryloyl or methacryloyl groups and one or more bicyclo[2.2.1]hept-2-ene structures.

SUMMARY OF THE INVENTION

One aspect of this invention accordingly provides a process for production of an image which comprises (1) exposing to actinic radiation a layer, supported on a carrier, of a liquid composition containing a compound (A) having in the same molecule both at least one group of formula

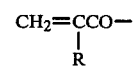

I and at least one group of formula

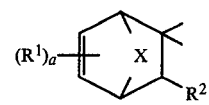

II such that the layer solidifies and becomes essentially nontacky due to photopolymerisation of (A) through the group or groups of formula I but remains substantially photocrosslinkable, and subsequently, when desired, (2) exposing as through an image-bearing transparency consisting of substantially opaque and substantially transparent areas at least part of the layer so solidified to a substantially greater amount of actinic radiation such that the further exposed part or parts of the photopolymerised layer undergo photocrosslinking through the group or groups of formula II, and (3) developing the image by dissolving in a solvent parts of the layer which have not become substantially photocrosslinked, where R denotes a hydrogen atom or a methyl group, a is zero or an integer of from 1 to 4, $R^1$ denotes a methyl group, or, if a is 1, may alternatively denote an allyl group, $R^2$ denotes a hydrogen atom, a carboxyl group, a carbonyloxyalkyl group (which may be interrupted in the chain by an ether oxygen atom), a carbonyloxyalkylene group joined through an oxygen atom to a group of formula I, the alkyl or alkylene group having up to 8 carbon atoms, or, together with one of the indicated free valencies, $R^2$ denotes a cyclic imide group of structure

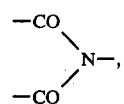

and

X denotes either a methylene bridge (which may be substituted by one or two of the aforesaid methyl groups $R^1$ or by the allyl group $R^1$) or an oxygen atom.

The expression "exposing as through an image-bearing transparency consisting of substantially opaque and substantially transparent parts" includes subjecting to a laser beam moved in a predetermined pattern directed by a computer so as to form an image.

For convenience, compounds containing at least one group of formula II are herein referred to as bicyclo[2.2.1]hept-2-enes, i.e., the 7-oxa analogues are included in the term unless the context forbids this.

It is known that norbornene (i.e., bicyclo[2.2.1]hept-2-ene) dimerises on exposure to actinic radiation (Photochemistry, by D. R. Arnold et al., published by Academic Press, 1974, at p. 170). It is further commonly known that acrylate and methacrylate esters undergo photopolymerisation on such irradiation. However, it is believed that preparing an image by a two-stage photopolymerisation and crosslinking process involving a compound having in the same molecule at least one group of formula I and at least one group of formula II is new.

DETAILED DISCLOSURE

Usually, the compound (A) employed in the process of this invention will contain, per average molecule, up to four groups of formula I, and preferably up to four groups of formula II. Generally it has a molecular weight of at most 10,000 and preferably at most 2,000. Preferably the group or groups of formula I, and preferably also the group or groups of formula II, are each directly attached to an atom or atoms of carbon, oxygen, or nitrogen.

Compounds containing at least one group of formula II, where $R^2$ denotes a hydrogen atom, suitable for use as (A) may be obtained by reaction, simultaneously or in either order, of a compound having two or more glycidyl groups directly attached to an atom or atoms of oxygen, nitrogen, or sulphur with acrylic or methacrylic acid and with a bicyclo[2.2.1]hept-2-ene-6-carboxylic acid of formula

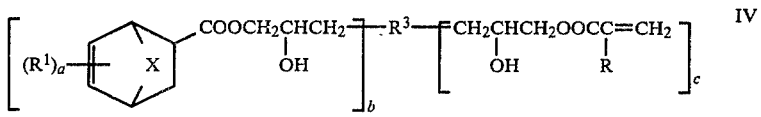

where $R^1$, X, and a have the meanings previously assigned, with the opening of the epoxide rings in the glycidyl groups.

There may thus be used as compound (A) substances of formula $$\left[(R^1)_a \underset{X}{\bigcirc} \overset{COOCH_2CHCH_2}{\underset{OH}{|}}\right]_b \left[R^3 \left[\begin{array}{c} CH_2CHCH_2OOCC=CH_2 \\ | \quad\quad\quad\quad\quad | \\ OH \quad\quad\quad R \end{array}\right]_c\right] \quad IV$$

where b and c are each independently an integer of at least 1 and preferably at most 4, R, $R^1$, X, and a have the meanings previously assigned, and $R^3$ denotes the residue of a compound containing at least (b+c) glycidyl groups directly attached to an atom or atoms of oxygen, nitrogen, or sulphur, after removal of (b+c) such glycidyl groups.

It will be appreciated that, due to competition for the epoxide groups, the product will also contain adducts formed from the compound having two or more glycidyl groups and from acrylic acid or methacrylic acid only, or from the compound containing two or more glycidyl groups and from the bicyclo [2.2.1]hept-2-ene-6-carboxylic acid only, i.e., compounds of formula $$\left[\begin{array}{c} CH_2 \!-\! CHCH_2 \\ \diagdown\!\!\diagup \\ O \end{array}\right]_d \left[R^3 \left[\begin{array}{c} CH_2CHCH_2OOCC=CH_2 \\ | \quad\quad\quad\quad\quad | \\ OH \quad\quad\quad R \end{array}\right]_e\right] \quad V$$

and compounds of formula $$\left[\begin{array}{c} CH_2\!-\!CHCH_2 \\ \diagdown\!\!\diagup \\ O \end{array}\right]_d \left[R^3 \left[\begin{array}{c} CH_2CHCH_2OOC \\ | \\ OH \end{array} \underset{X}{\bigcirc}\!\!-\!(R^1)_a \right]_e\right] \quad V$$

where d represents zero or a positive integer, e is an integer of at least one, the sum of (d+e) being the same as the sum of (b+c), and R, $R^1$, $R^3$, X, and a have the meanings assigned above.

The extent of formation of the byproducts of formula V or VI will depend, of course, on the proportion of the three types of reactants employed. In general, the presence of such byproducts does not interfere with the carrying out of the process of this invention.

As examples of compounds containing glycidyl groups which may be treated with acrylic acid or methacrylic acid and with a bicyclo[2.2.1]hept-2-ene-6-carboxylic acid of formula III may be mentioned polyglycidyl esters obtainable by reaction of a compound containing two or more carboxylic acid groups per molecule with epichlorohydrin or with glycerol dichlorohydrin in the presence of an alkali. Such polyglycidyl esters may be derived from aliphatic polycarboxylic acids, e.g., succinic acid, glutaric acid, adipic acid, pimelic acid, suberic acid, azelaic acid, sebacic acid, or dimerised or trimerised linoleic acid; from cycloaliphatic polycarboxylic acids such as tetrahydrophthalic acid, 4-methyltetrahydrophthalic acid, hexahydrophthalic acid, and 4-methylhexahydrophthalic acid, and from aromatic polycarboxylic acids such as phthalic acid, isophthalic acid, and terephthalic acid. Other suitable polyglycidyl esters are obtainable by polymerisation of glycidyl esters of vinylic acids, especially glycidyl acrylate and glycidyl methacrylate.

Further examples are polyglycidyl ethers obtainable by reaction of a compound containing at least two free alcoholic hydroxyl and/or phenolic hydroxyl groups per molecule with epichlorohydrin under alkaline conditions or, alternatively, in the presence of an acidic catalyst and subsequent treatment with alkali. These ethers may be made from acyclic alcohols such as ethylene glycol, diethylene glycol, and higher poly(oxyethylene) glycols, propane-1,2-diol and poly(oxypropylene) glycols, propane-1,3-diol, poly(oxytetramethylene) glycols, pentane-1,5-diol, hexane-2,4,6-triol, glycerol, 1,1,1-trimethylolpropane, pentaerythritol, sorbitol, and polyepichlorohydrins; from cycloaliphatic alcohols such as resorcitol, quinitol, bis(4-hydroxycyclohexyl)methane, 2,2-bis(4-hydroxycyclohexyl)propane, and 1,1-bis(hydroxymethyl)cyclohex-3-ene; and from alcohols having aromatic nuclei, such as N,N-bis(2-hydroxyethyl)aniline and p,p'-bis(2-hydroxyethylamino)diphenylmethane. Or they may be made from mononuclear phenols, such as resorcinol and hydroquinone, and from polynuclear phenols, such as bis(4-hydroxyphenyl)methane (otherwise known as bisphenol F), 4,4'-dihydroxydiphenyl, bis(4-hydroxyphenyl) sulphone, 1,1,2,2-tetrakis(4-hydroxyphenyl)ethane, 2,2-bis(4-hydroxyphenyl)propane (otherwise known as bisphenol A), 2,2-bis(3,5-dibromo-4-hydroxyphenyl)propane, and novolaks formed from aldehydes such as formaldehyde, acetaldehyde, chloral, and furfuraldehyde, with phenol itself, and phenol substituted in the ring by chlorine atoms or by alkyl groups each containing up to nine carbon atoms, such as 4-chlorophenol, 2-methylphenol, and 4-tert.-butylphenol.

Poly(N-glycidyl) compounds may also be used, e.g., N-glycidyl derivatives of amines such as aniline, n-butylamine, bis(4-aminophenyl)methane, and bis(4-methylaminophenyl)methane; triglycidyl isocyanurate; and N,N'-diglycidyl derivatives of cyclic alkylene ureas, such as ethyleneurea and 1,3-propyleneurea, and of hydantoins such as 5,5-dimethylhydantoin.

Poly(S-glycidyl) compounds may also be used, e.g., di(S-glycidyl) derivatives of dithiols such as ethane-1,2-dithiol and bis(4-mercaptomethylphenyl) ether, but they are not preferred.

Polyepoxides having the 1,2-epoxide groups attached to different kinds of hetero atoms may be employed, e.g., the glycidyl ether-glycidyl ester of salicyclic acid, or p-(diglycidylamino)phenyl glycidyl ether.

Most preferably $R^3$ represents the divalent residue of a diglycidyl ether, which may have been advanced, of a dihydric phenol or of a dihydric aliphatic alcohol.

Compounds containing at least one group of formula II, where $R^2$ denotes a hydrogen atom, suitable for use as (A) may also be obtained by a similar reaction between a bicyclo[2.2.1]hept-2-ene-6-carboxylic acid of formula III and glycidyl acrylate or glycidyl methacrylate. Such compounds are of formula

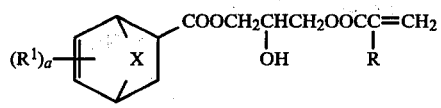

VII where R, $R^1$, X, and a have the meanings previously assigned.

Methods of bringing about the ring-opening of 1,2-epoxide groups with carboxylic acids are well known.

Compounds containing at least one group of formula II, where $R^2$ denotes a hydrogen atom, suitable for use as component (A) may also be obtained by esterification of a compound containing two or more alcoholic or phenolic hydroxyl groups with acryloyl or methacryloyl chloride and with a bicyclo[2.2.1]hept-2-ene-6-carboxylic acid chloride of formula

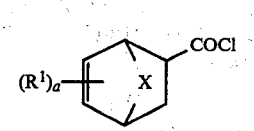

VIII where $R^1$, X, and a have the meanings previously assigned.

There may accordingly be used esters of the formula

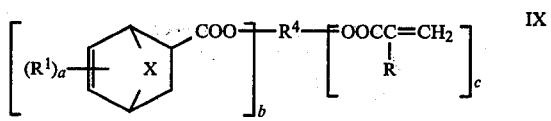

IX where
  R, $R^1$, X, a, b, and c have the meanings previously assigned, and
  $R^4$ denotes the residue, after removal of (b+c) alcoholic or phenolic hydroxyl groups respectively, of an alcohol having at least (b+c) alcoholic hydroxyl groups or of a phenol having at least (b+c) phenolic hydroxyl groups.

$R^4$ preferably denotes an aliphatic residue comprising repeating units of formula $-O(CH_2)_f-$ or $-CO(CH_2)_5O-$, (where f represents 2, 3, or 4) or repeating units of formula $-CH_2CH(OH)-$. Thus, $R^4$ may, for example, represent the residue of a polyoxyethylene glycol or polyoxypropylene glycol of average molecular weight 250 to 5000, or the residue of a polyvinyl alcohol of average molecular weight 500 to 9000.

It will be understood that there will similarly be formed byproducts of formula

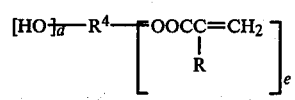

X and byproducts of formula

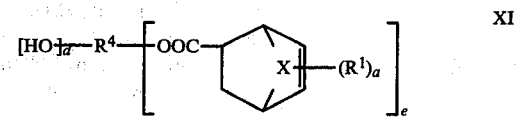

XI where R, $R^1$, $R^4$, X, a, d, and e have the meanings previously assigned. In general they do not, however, interfere with the process of this invention.

Esters similar to those of formula IX, also suitable for use as component (A), are of formula

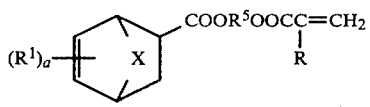

where
R, R¹, X, and a have the meanings previously assigned and
R⁵ denotes an alkylene group of 2 to 6 carbon atoms, and may be obtained by esterification of a hydroxyalkyl (meth)acrylate of formula

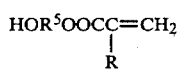

such as 2-hydroxyethyl acrylate or 2-hydroxypropyl methacrylate, with a bicyclo[2.2.1]hept-2-ene-6-carboxylic acid chloride of formula VIII.
Amides of formula

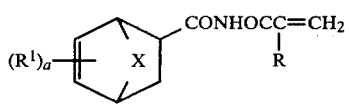

where R, R¹, X, and a have the meanings previously assigned, suitable for use as (A), may be obtained by treatment of (meth)acrylamide with a bicyclo[2.2.1-]hept-2-ene-6-carboxylic acid chloride of formula VIII or by reaction of (meth)acryloyl chloride and a bicyclo[2.2.1]hept-2-ene-6-carboxamide of formula

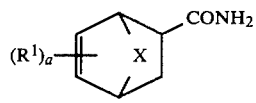

where R¹, X, and a have the meanings previously assigned.

Similarly, reaction of a bicyclo[2.2.1]hept-2-ene-6-carboxylic acid chloride of formula VIII with an N-hydroxymethyl(meth)acrylamide yields amides, suitable for use as (A), of formula

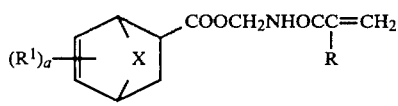

where R, R¹, X, and a have the meanings previously assigned.

Other esters containing a group of formula II, where R² denotes a hydrogen atom and suitable for use as (A), are obtainable by the esterification with (meth)acryloyl chloride of a bicyclo[2.2.1]hept-2-en-6-ol or a 6-hydroxymethylbicyclo[2.2.1]hept-2-ene; they are of formula

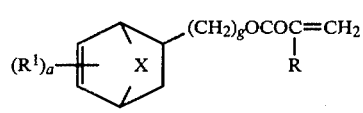

where
R, R¹, X, and a have the meanings assigned above and
g is zero or 1.

There also come into consideration amides prepared by the reaction of a polyamine, simultaneously or in either sequence, with (meth)acryloyl chloride and a bicyclo[2.2.1]hept-2-ene-6-carboxylic acid chloride of formula VIII, i.e., amides of formula

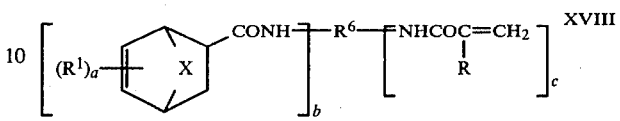

where
R, R¹, X, a, b, and c have the meanings previously assigned and
R⁶ denotes the residue of a compound containing at least (b+c) primary amino groups, after removal of (b+c) such amino groups.

Likewise, there will be formed byproducts of formula

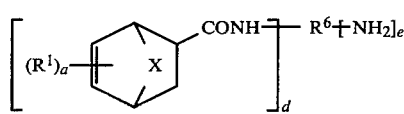

or

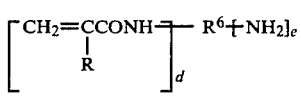

where R, R¹, R⁶, X, a, d, and e have the meanings previously assigned, but they do not in general interfere.

Preferably R⁶ represents the residue of an alkylenediamine of 2 to 8 carbon atoms, of a phenylenediamine, or a bis(aminophenyl)methane after removal of both primary amino groups.

A further route comprises reaction of alcohols of formula

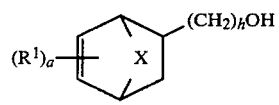

where
h is 0, 1, or 2 and
R¹, X, and a have the meanings previously assigned, with a diacid chloride of formula ClCOR⁷COCl, where R⁷ denotes a carbon-carbon bond or a divalent group of 1 to 10 carbon atoms, and with a hydroxyalkyl (meth)acrylate of formula XIII.

There thus come into consideration esters of formula

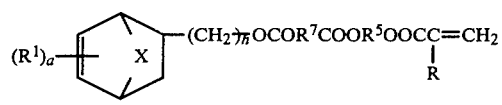

where R, R¹, R⁵, R⁷, X, a, and h have the meanings previously assigned.

Byproducts of formula

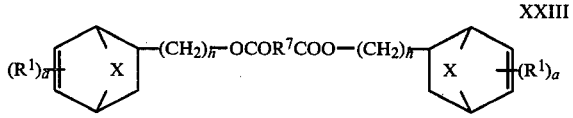

and of formula

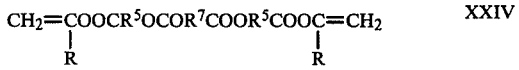

where R, $R^1$, $R^5$, $R^7$, X, a, and h have the meanings previously assigned, are also formed, but do not in general interfere.

Compounds containing a group of formula II, where $R^2$ denotes a hydrogen atom, and suitable for use as (A), may be also obtained by reaction of a 6-hydroxymethyl-bicyclo [2.2.1]hept-2-ene with glycidyl (meth)acrylate under ring-opening conditions. The resultant 3-(meth)acryloyloxy-2-hydroxypropoxymethyl derivatives are of formula

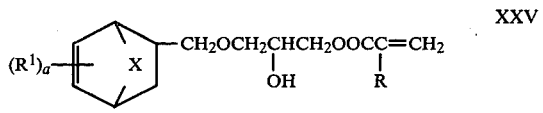

where R, $R^1$, X, and a have the meanings previously assigned.

There may also be used carbonates of formula

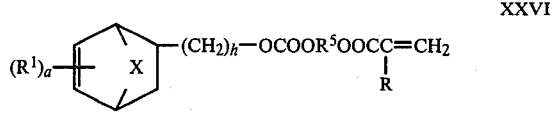

where R, $R^1$, $R^5$, X, a, and h have the meanings previously assigned, obtainable by reaction of an alcohol of formula XXI and a hydroxyalkyl (meth)acrylate of formula XIII with an excess of phosgene. There may also be formed as byproducts the carbonates of formula

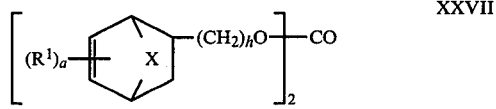

and of formula

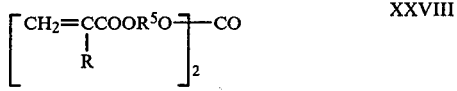

where R, $R^1$, $R^5$, X, a, and h have the meanings assigned above, but they do not in general interfere with the process of this invention.

Further compounds suitable for use as (A) are the diurethanes of formula

obtainable by reaction of a di-isocyanate with an alcohol of formula XXI and a hydroxyalkyl acrylate of formula XIII, where R, $R^1$, $R^5$, X, a, and h have the meanings previously assigned and $R^8$ represents the residue, after removal of the two isocyanate groups, of an organic di-isocyanate, and is preferably an arylene or aralkylene group of 6 to 15 carbon atoms.

Diurethanes of formula

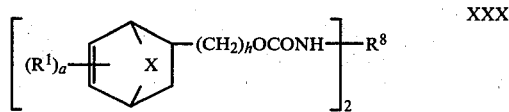

and of formula

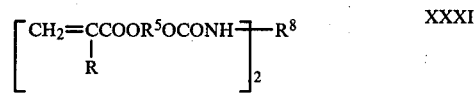

where R, $R^1$, $R^5$, $R^8$, X, a, and h have the meanings previously assigned, may be formed as byproducts but do not in general interfere with the carrying out of the process of this invention.

Other routes to compounds containing at least one group of formula II where $R^2$ denotes a hydrogen atom and suitable for use as (A) involve a bicyclo[2.2.1]hept-2-en-6-al as intermediate.

Thus, such an aldehyde may be converted into a 6,6-bis(hydroxymethyl)bicyclo[2.2.1]hept-2-ene by reaction with formaldehyde and this diol may be converted directly into a (meth)acrylate of formula

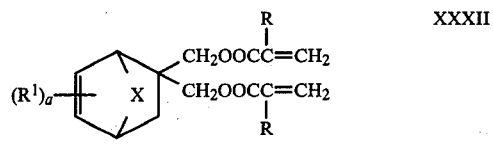

where R, $R^1$, X, and a have the meanings assigned above, by esterification with 2 mol. of (meth)acryloyl chloride, or it may be converted into a diglycidyl ether which may then be caused to react with (meth)acrylic acid to afford a diester of formula

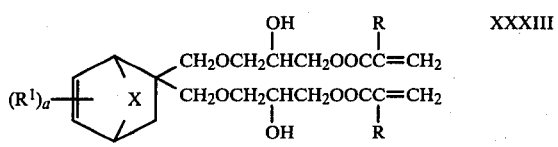

where R, $R^1$, X, and a have the meanings previously assigned.

Or a bicyclo[2.2.1]hept-2-en-6-al may be caused to react with an at least trihydric alcohol to form an acetal and at least one residual alcoholic group is esterified with (meth)acryloyl chloride, in either sequence, to yield ester-acetals of formula

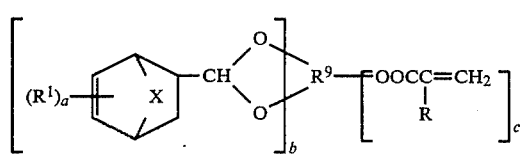     XXXIV where
R, R¹, X, a, b, and c have the meanings previously assigned and
R⁹ denotes the residue of a compound containing at least (2b+c) alcoholic hydroxyl groups, after removal of (2b+c) such hydroxyl groups, such as a polyvinyl alcohol of average molecular weight 500 to 9000.

It will be understood that byproducts containing groups of formula I but none of formula II, or vice versa, may be formed, that is to say, compounds of

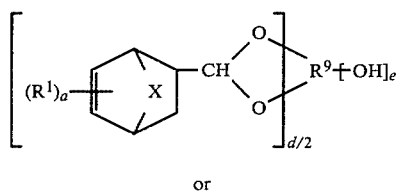     XXXV or

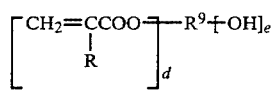     XXXVI where R, R¹, R⁹, X, a, d, and e have the meanings previously assigned, but, in general, such byproducts do not interfere with the process of this invention.

Phosphorous-containing compounds, suitable for use as (A), are of formula

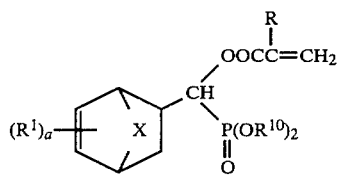     XXXVII and are obtainable by reaction of a bicyclo[2.2.1]hept-2-en-6-al with a phosphonate of formula $(R^{10}O)_2PHO$ to afford the alcohol of formula

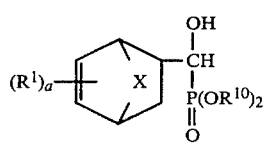     XXXVIII followed by esterification with (meth)acryloyl chloride, where
R, R¹, X, and a have the meanings previously assigned and
each R¹⁰ denotes an alkyl group of 1 to 6 carbon atoms, which may be interrupted by one or two oxygen atoms, an alkenyl group of 2 to 6 carbon atoms, a cycloalkyl group of 5 to 7 carbon atoms, an aryl group of 6 to 9 carbon atoms, or an aralkyl group of 7 to 10 carbon atoms.

Yet further intermediates useful in the preparation of compounds containing at least one group of formula II where R² is other than a hydrogen atom and suitable for use as (A), are bicyclo[2.2.1]hept-2-ene-5,6-dicarboxylic acid anhydrides. They may be caused to react with a hydroxyalkyl (meth)acrylate of formula XIII to afford an acid ester of formula

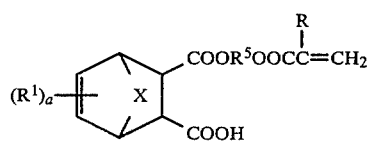     XXXIX where R, R¹, R⁵, X, and a have the meanings previously assigned.

If desired, such acid esters may be further esterified by aliphatic alcohols of up to 7 carbon atoms, optionally containing an ether oxygen atom in the chain, e.g. 2-n-butoxyethanol.

Or such an anhydride may be converted into the 5,6-dicarboxylic acid which may similarly be esterified with a hydroxyalkyl (meth)acrylate of formula XIII (2 mol.) to yield a diester of general formula

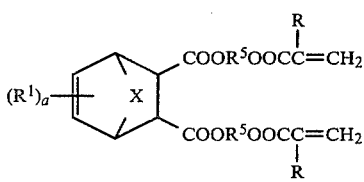     XL where R, R¹, R⁵, X, and a have the meanings previously assigned.

Other routes to compounds, suitable for use as (A), from bicyclo[2.2.1]hept-2-ene-5,6-dicarboxylic anhydrides involve forming a half-ester with a monohydric alcohol of formula R¹¹OH and then either converting it into an acid chloride (by reaction with e.g., thionyl chloride) and then esterifying this with a hydroxyalkyl (meth)acrylate of formula XIII, or treating the half-ester with glycidyl (meth)acrylate to form the 3-(meth)acryloyl-2-hydroxypropyl ester.

There thus come into consideration compounds of formula

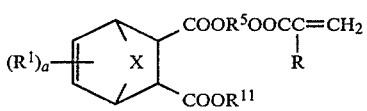     XLI or of formula

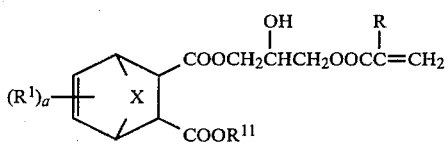     XLII where
R, R¹, R⁵, X, and a have the meanings previously assigned, and $R^{11}$ denotes an alkyl group of 1 to 8 carbon atoms, optionally interrupted in the chain by an ether oxygen atom.

Still further compounds, suitable for use as (A), are substituted imides of formula

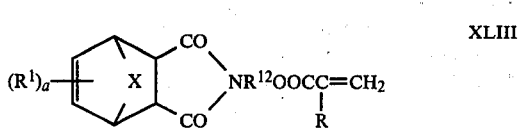

XLIII where

R, $R^1$, X, and a have the meanings previously assigned and $R^{12}$ denotes an alkylene group of 1 to 6 carbon atoms.

Such compounds are obtainable from bicyclo[2.2.1-]hept-2-ene-5,6-dicarboxylic acid anhydrides, either by conversion into the imide then reaction with formaldehyde to give the N-methylolimide, or by reaction with an aminoalcohol of formula $NH_2R^{12}OH$, followed in each case by esterification with (meth)acryloyl chloride.

Particularly preferred as (A) are compounds containing a group of formula II in which a is 1 or zero denotes an unsubstituted methylene bridge, i.e., $-CH_2-$.

Intermediates required for preparing compounds of formulae IV, VII, IX, XII, XIV, XVI–XVIII, XXII, XXV, XXVI, XXIX, XXXII to XXXIV, XXXVIII and XXXIX to XLIII are, in general, well known (see e.g., British Patent Specification No. 935,756), being commonly made by a Diels-Alder reaction between cyclopentadiene or furan, which may be substituted by up to 4 methyl groups or by an allyl group, and a suitable dienophile such as acrylic acid, acrolein, or maleic anhydride. Several of those derived from cyclopentadiene are commercially available.

Specific examples of substances suitable for use as (A) are 3-(methacryloyloxy)-2-hydroxypropyl bicyclo[2.2.1]hept-2-ene-6-carboxylate, 2-(acryloyloxy)ethyl methyl-5-carboxybicyclo[2.2.1]hept-2-ene-6-carboxylate and the corresponding methacryloyloxy compound, 2-(acryloyloxy)ethyl 5-carboxy-7-oxabicyclo[2.2.1]hept-2-ene-6-carboxylate, 2-(acryloyloxy)propyl allyl-5-carboxybicyclo[2.2.1]hept-2-ene-6-carboxylate, 3-(methacryloyloxy)-2-hydroxypropyl methyl-5-carbomethoxybicyclo[2.2.1]hept-2-ene-6-carboxylate, 2-(methacryloyloxy)ethyl 5-carboxy-7-oxabicyclo[2.2.1]hept-2-ene-6-carboxylate, and N-(2-methacryloyloxy)ethyl methylbicyclo[2.2.1]hept-2-ene-5,6-dicarboxyimide.

The second of these compounds is prepared from methylbicyclo[2.2.1]hept-2-ene-5,6-dicarboxylic acid anhydride, which is in turn prepared by a Diels-Alder reaction between methylcyclopentadiene and maleic anhydride. It will be appreciated that no specific location can be assigned for the methyl group in methylcyclopentadiene, since the commercial product consists of mixtures which may isomerise. From this, it follows that specific locations cannot be assigned in the adduct with maleic anhydride either, nor, of course, in derivatives of the bicyclo[2.2.1]hept-2-ene-5,6-dicarboxylic anhydride so produced. The same applies to homologues used in the process of this invention, containing up to four methyl groups in the bicyclo[2.2.1]hept-2-ene nucleus. Similarly, no specific location can be assigned to the allyl group in allylcyclopentadiene, from which compounds containing at least one group of formula II where $(R^1)_a$ denotes an allyl group may be prepared.

For photopolymerisation through groups of formula I it is greatly preferred that the liquid composition contain an added photoinitiator, i.e., a catalyst which, on irradiation, gives an excited state that leads to formation of free radicals which then initiate polymerisation of (A). Examples of suitable photoinitiators are organic peroxides and hydroperoxides, α-halogen substituted acetophenones such as trichloromethyl 4'-tert. butylphenyl ketone, α-hydroxy-α-alkyl-substituted acetophenones such as 2-hydroxy-2-methyl-1-phenylpropan-1-one, benzoin and its alkyl ethers (e.g., the n-butyl ether), α-methylbenzoin, alkyl, α,α-dialkoxy-α-benzoylacetates, benzophenones such as benzophenone itself and 4,4'-bis(dimethylamino)benzophenone, O-alkoxycarbonyl derivatives of an oxime of benzil or of 1-phenylpropane-1,2-dione, such as benzil (O-ethoxycarbonyl)-α-monoxime and 1-phenylpropane-1,2-dione 2-(O-ethoxycarbonyl)oxime, benzil ketals, e.g., its dimethyl ketal, substituted thioxanthones, e.g., 2-chlorothioxanthone, anthraquinones, esters of phenylglyoxylic acid, 2-benzoyl-2-phenyl-1,3-dioxolanes and 4-benzoyl-4-phenyl-1,3-dioxolanes, and photoredox systems comprising a mixture of a phenothiazine dye (e.g., methylene blue) or a quinoxaline (e.g., a metal salt of 2-(m- or p-methoxyphenyl)quinoxaline-6' or 7'-sulphonic acid) with an electron donor such as benzenesulphinic acid or other sulphinic acid, or a salt of a sulphinic acid, e.g., the sodium salt, or an arsine, a phosphine, or thiourea.

Suitable photoinitiators are readily found by routine experimentation. Generally, 0.15 to 10%, and preferably 2.5 to 5% by weight of the photoinitiator is incorporated, based on the total weight of (A) and any further compound (B) present containing at least one group of formula I but none of formula II. (Substances suitable for use as compound (B) are described below.)

References in this Specification to photocrosslinking through groups of formula II are not to be construed as precluding the possibility that a minor amount of photodimerisation in stage (1) may take place through groups of formula II: it is believed, however, that the great preponderance of photopolymerisation in stage (1) involves only groups of formula I.

As stated above, the composition is applied in a liquid form to a carrier. Conveniently its viscosity is in the range 0.1 to 0.4 Pa s. To meet the requirement that the composition be liquid it may be necessary, in order to achieve this without the use of volatile organic solvents, to include another compound which is a liquid and which photopolymerises under the conditions in stage (1) to form a solid. It is convenient to use for the purpose a photopolymerisable compound (B) having in the molecule at least one group of formula I but none of formula II. Compound (B) may be, for example, an alkyl or hydroxyalkyl ester (which alkyl or hydroxyalkyl group may be substituted) of acrylic acid or methacrylic acid, typically, such esters having up to 15 carbon atoms in all, such as methyl methacrylate, ethyl methacrylate, n-butyl acrylate, and 2-hydroxyethyl acrylate. Also useful for this purpose are 3-alkoxy-2-hydroxypropyl, 3-alkenoxy-2-hydroxypropyl, and 3-aryloxy-2-hydroxypropyl esters of acrylic acid or methacrylic acid, typically those containing up to 15 carbon atoms in all.

Other kinds of compound (B) may be included in the liquid composition so that some desired property may be imparted to the photopolymerised, photocrosslinked product. Thus, to impart flame-retardant properties the compound (B) may also contain at least one chlorine, bromine, or phosphorus atom. Examples of such are adducts of acrylic acid or methacrylic acid with a bromine- or chlorine-substituted aryl glycidyl ether such as a dibromo-p-cresyl glycidyl ether, e.g., 3-(methacryloyloxy)-2-hydroxypropyl, X,Y-dibromo-p-cresyl ether.

It has been found advantageous further to incorporate in the liquid composition as a compound (B) one which has in the molecule at least one group of formula

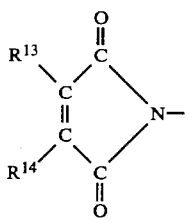  XLIV where $R^{13}$ and $R^{14}$, which may be the same or different, each denote an alkyl group of 1 to 4 carbon atoms or together they denote a trimethylene or tetramethylene group which may be optionally substituted by a methyl group. The presence of such a compound generally results in improved adhesion of the photocrosslinked product to the substrate.

Compounds having in the molecule both at least one group of formula XLIV and at least one group of formula I are described in British Patent Specification No. 1,544,840. Usually the compound will contain, per average molecule, up to four groups of formula XLIV and up to four groups of formula I. Preferably it has a molecular weight of at most 10,000, and preferably the group or groups of formula XLIII and the group or groups of formula I are each directly attached to an atom or atoms of carbon, oxygen, or nitrogen. Particularly preferred are such compounds where $R^{13}$ and $R^{14}$ in formula XLIV each represent a methyl group.

Such compounds may be of formula

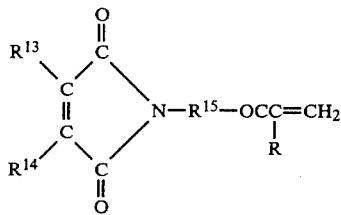  XLV where
R, $R^{13}$, and $R^{14}$ have the meanings assigned above and
$R^{15}$ denotes an imino group, an alkylenoxy group of 1 to 10 carbon atoms (which may be substituted on a carbon atom thereof by a hydroxyl group), a cycloalkyleneoxy group of 5 to 7 carbon atoms, or an alkylenecarbonamido group of 2 to 10 carbon atoms.

$R^{15}$ may represent, for example, an alkylenecarbonamido group of formula $-(CH_2)_5CONH-$, an alkylenoxy group of formula $-(CH_2)_6O-$, a cyclohexyleneoxy group, or a methylcyclohexyleneoxy group; preferably it denotes a group of formula $-(CH_2)_jO-$, $-CH_2CH(CH_3)O-$, or $-CH_2CH(OH)CH_2O-$, where j denotes 1, 2, or 3.

Compounds of formula XLV where $R^{15}$ denotes an imino group may be obtained from an N-amino-2,3-disubstituted maleimide by treatment with acryloyl chloride or methacryloyl chloride.

Compounds of formula XLV where $R^{15}$ denotes an alkeneoxy group of at least 2 carbon atoms may be obtained by reaction of a 2,3-disubstituted maleic anhydride with an aminoalcohol followed by treatment with acryloyl chloride or methacryloyl chloride, while those where $R^{15}$ denotes $-CH_2O-$ may be obtained by conversion of a 2,3-disubstituted maleimide into its N-hydroxymethyl derivative by means of formaldehyde, followed by treatment with (meth)acryloyl chloride. Such compounds where $R^{15}$ represents $-CH_2CH(OH)CH_2O-$ may be obtained by reaction of an N-glycidyl-2,3-disubstituted maleimide with acrylic acid or methacrylic acid. Compounds of formula XLV where $R^{15}$ denotes a cycloalkeneoxy group may be obtained by reaction of a 2,3-disubstituted maleic anhydride with a cycloaliphatic aminoalcohol followed by treatment with acryloyl chloride or methacryloyl chloride.

Compounds of formula XLV where $R^{15}$ denotes an alkylenecarbonamido group may be obtained by reaction of a 2,3-disubstituted maleic anhydride with an amino-substituted aliphatic carboxylic acid to form the N-(carboxyalkylene)-2,3-disubstituted maleimide, conversion into the acid chloride, and reaction with acrylamide or methacrylamide.

Specific examples of such substances are N-(2-acryloyloxy)ethyl-2,3-dimethylmaleimide, N-(3-(acryloyloxy)-2-hydroxypropyl)-2,3-dimethylmaleimide, (N-(3-(acryloyloxy)propyl)-2,3-dimethylmaleimide, and the corresponding methacryloyl homologues.

As is explained below, it may be desirable to introduce epoxide groups into the composition: after the product has been photocrosslinked, additional cross-linking may be achieved by thermal curing through epoxide groups. It may therefore be advantageous to include in the liquid composition a photopolymerisable compound having in the same molecule both a group of formula I and only one 1,2-epoxide group, such as glycidyl acrylate or glycidyl methacrylate. Alternatively, an epoxide resin (i.e., a compound containing more than one epoxide group) may be included in the liquid composition before photopolymerisation.

If desired the liquid composition may likewise contain a photopolymerisable compound (C) having at least one group of formula II but none of I, e.g., bicyclo[2.2.1]hept-2-ene.

The liquid composition can be applied to suitable carriers by the customary techniques, such as spray coating, whirler coating, roller coating, cascade coating, and especially curtain coating. Typically, the carrier is coated such that the layer of the composition is 1 to 250 μm thick. The carrier may be of, for example, copper, aluminium or other metal, paper, synthetic resin, or glass.

In both the photopolymerising and the subsequent photocrosslinking stage of the process of this invention actinic radiation of wavelength 200–600 nm is preferably used. Suitable sources of actinic radiation include carbon arcs, mercury vapour arcs, fluorescent lamps with phosphors emitting ultraviolet light, argon and xenon glow lamps, tungsten lamps, and photographic flood lamps. Of these, mercury vapour arcs, particularly sun lamps, fluorescent sun lamps, and metal halide lamps are most suitable. The times required for the exposures of the photopolymerisable composition and the still photocrosslinkable composition will depend upon a variety of factors which include, for example, the individual compounds used, the type of light source, and the distance of that source from the irradiated composition. Suitable times may be readily determined by those familiar with photopolymerisation techniques; usually the amount of light energy required in the second stage (the photocrosslinking stage) is 15 to 100 times that required in the first stage, typically, 25 to 60 times. By way of example, the composition is first irradiated at a distance of 10–25 cm from a source of irradiation for 2–15 seconds: in the second stage it is irradiated for 10–20 minutes at a distance of 15–30 cm.

The preferred substances for use as compound (A) contain only one group of formula I per molecule, but satisfactory results have been achieved with substances containing more than one such group. Where diacrylates, dimethacrylates and other substances containing more than one group of formula I are used, exposure to actinic radiation in stage (1) should be restricted so that any crosslinking in that stage through groups of formula I does not proceed to an extent such that formation of an image in stage (3) is substantially inhibited.

Suitable solvents for development of the image are readily found by routine testing and include cyclohexanone, trimethylcyclohexanone, 2-ethoxyethanol, 1,1,1-trichloroethane, and mixtures thereof. The action of the solvent may need to be assisted by agitation or by gentle brushing. When the carrier has a layer of a suitable electrically-conducting metal, usually copper or silver, immediately in contact with the photopolymerised composition the uncrosslinked polymer (if any) can be removed to expose the metal. Metal so exposed may then be etched away in the non-image areas, so forming a printed circuit, by means of etching fluids such as ferric chloride or ammonium persulphate solutions.

If desired, it is possible to include in the liquid composition a compound (B) which also has at least one free sulphonic or phosphoric acid group, or particularly at least one free carboxylic acid group; conveniently, this is acrylic acid or methacrylic acid or an adduct of a hydroxyalkyl acrylate or methacrylate of formula XIII with trimellitic anhydride, i.e., an adduct of formula

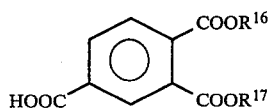  XLVI where either $R^{16}$ denotes a hydrogen atom, in which case $R^{17}$ denotes a group of formula

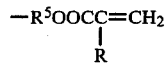  XLVII or $R^{16}$ denotes a group of formula XLVII in which case $R^{17}$ denotes a hydrogen atom,
wherein R and $R^5$ have the meanings previously assigned.

In place of, or as well as, such a compound (B) there may be used a carboxyl-containing compound (A) of formula XXXIX.

The presence of free sulphonic, phosphoric, or carboxylic acid groups in the photopolymerised polymer has as a consequence the facility of using an aqueous solution of a base, such as dilute sodium hydroxide, sodium carbonate, disodium hydrogen orthophosphate, or ammonia solutions, for development of the image, thus avoiding the use of organic solvents in this stage.

Alternatively, there may be included in the liquid composition a compound (B) which also has at least one primary, secondary, or tertiary amino group. As a consequence of the presence of free amino groups in the photopolymerised polymer, aqueous solutions of acids may be used for development of the image, such as dilute solutions of acids, particularly mineral acids. Examples of such compounds (B) are alkyl esters of acrylic or methacrylic acid, which alkyl groups are substituted by a secondary or tertiary amino group, such as 2-(dimethylamino)ethyl methacrylate.

As has already been indicated, the composition after photopolymerisation and photocrosslinking may contain an epoxide resin in which case it may also contain a latent, heat-curing agent for the epoxide resin so that the composition may be heated and supplementary crosslinking occur, further to increase the resistance of the photocrosslinked product to solvents and high temperatures. The epoxide resin may, as already stated, be included as such in the composition or may be formed in situ through photopolymerisation of a compound (B) which also contains in the same molecule only one 1,2-epoxide group. Examples of latent, heat-curing agents for epoxide resins are polycarboxylic acid anhydrides, such as hexahydrophthalic anhydride, dicyandiamide, complexes of amines such as ethylamine, trimethylamine, and n-octyldimethylamine with boron trifluoride or with boron trichloride, latent boron difluoride chelates, aromatic polyamines such as bis(p-aminophenyl)methane and bis(p-aminophenyl) sulphone, aromatic biguanides such as 2,6-xylidene biguanide, and imidazoles such as 2-ethyl-4-methylimidazole and 2-phenylimidazole. The latent heat-curing agent may also be a polycarboxylic acid, formed in situ by photopolymerisation of a monocarboxylic acid compound (B) or a compound (A) of formula XXXIX.

The following Examples illustrate the invention. Unless otherwise indicated, parts and percentages are by weight. Substances used in the Examples were prepared as follows:

3-(Methacryloyloxy)-2-hydroxypropyl bicyclo[2.2.1]hept-2-ene-6-carboxylate

Glycidyl methacrylate (43 g), containing 0.13 g of 2,6-di-tert. butyl-p-cresol and 0.26 g of tetramethylammonium chloride, was heated to 100° C. and bicyclo[2.2.1]hept-2-ene-6-carboxylic acid (41.8 g) was added slowly over about 1 hour, so that the temperature of the mixture did not exceed 105° C. Heating at 100° C. was continued for a further three hours, by which time the epoxide content of the product was negligible. The above-mentioned ester was a colourless mobile liquid.

2-(Acryloyloxy)ethyl methyl-5-carboxybicyclo[2.2.1]hept-2-ene-6-carboxylate

Methylbicyclo [2.2.1]hept-2-ene-5,6-dicarboxylic acid anhydride (40 g) and 2-hydroxyethyl acrylate (26 g) were heated in 250 ml of toluene at 100° C. for 3 hours, and then the toluene was distilled off under reduced pressure to leave the above-mentioned half ester as a viscous liquid.

2-(Methacryloyloxy)ethyl methyl-5-carboxybicyclo[2.2.1]hept-2-ene-6-carboxylate This was prepared similarly, from 2-hydroxyethyl methacrylate.

3-(Methacryloyloxy)-2-hydroxypropyl methyl-5-carbomethoxybicyclo-[2.2.1]hept-2-ene-6-carboxylate A mixture of methylbicyclo [2.2.1]hept-2-ene-5,6-dicarboxylic anhydride (50 g) and anhydrous methanol (200 ml) containing 0.02 g of N-benzyldimethylamine as catalyst was heated to reflux for 7 hours, and then the excess of methanol was distilled off under reduced pressure to leave methyl-5-carbomethoxybicyclo [2.2.1]hept-2-ene-6-carboxylic acid (yield, 59 g).

This acid ester (50 g) was heated with glycidyl methacrylate (40 g) at 100° C. in the presence of 0.27 g of tetramethylammonium chloride and 0.13 g of 2,6-di-tert.butyl-p-cresol until the epoxide content had fallen to a negligible level; the desired ester so formed was a viscous liquid.

2-(Acryloyloxy)ethyl 5-carboxy-7-oxabicyclo [2.2.1]hept-2-ene-6-carboxylate

Maleic anhydride (50 g) and furan (150 ml) were heated under reflux for 1 hour, and then the excess of furan was distilled off. The residue was recrystallised from chloroform, yielding 72 g of 7-oxabicyclo [2.2.1]hept-2-ene-5,6-dicarboxylic acid anhydride (m.pt. 110° C., decomp.). This anhydride (40 g) and 30.75 g of 2-hydroxyethyl acrylate were heated in 250 ml of toluene at 100° C. for 3 hours, and then the toluene was distilled off under reduced pressure, leaving the desired compound as a viscous liquid.

N-(2-Methacryloyloxy)ethyl) methylbicyclo [2.2.1]hept-2-ene-5,6-dicarboximide Ethanolamine (91.5 g) was added gradually with constant stirring to methylbicyclo [2.2.1]hept-2-ene-5,6-dicarboxylic acid anhydride (268.5 g) heated to 120°–125° C., and the mixture was then heated at that temperature for a total of 30 minutes. The product was cooled to room temperature, taken up in dichloromethane (750 ml), then washed with 1 N sodium hydroxide solution (150 ml), water (2 portions of 250 ml), dried over anhydrous magnesium sulphate, and then filtered. Evaporation of the solvent from the filtrate left 290 g (89%) yield of N-(2-hydroxyethyl) methylbicyclo [2.2.1]hept-2-ene-5,6-dicarboximide.

This imide (222 g), and triethylamine (111 g) which had been dried over sodium hydroxide, were dissolved in 470 ml of diethyl ether (dried over sodium) containing 0.2% of 2,6-di-tert.butyl-4-methylphenol. The solution was cooled to below 0° C., and methacryloyl chloride (105 g) was added dropwise, the temperature of the mixture being kept in the range −10° C. to −5° C. After the addition was complete stirring was continued and the mixture was allowed to warm to room temperature. After the precipitated triethylamine hydrochloride had been filtered off the filtrate was washed with 0.5 N hydrochloric acid (65 ml) and water (2×65 ml), then dried over anhydrous magnesium sulphate. On filtration and evaporation of the solvent there remained 213 g (73%) of the desired N-(methacryloyloxyethyl)imide as a golden orange oil.

2-(Methacryloyloxy)ethyl 5-carboxy-7-oxabicyclo [2.2.1]hept-2-ene-6-carboxylate A mixture of 7-oxabicyclo [2.2.1]hept-B 2-ene-5,6-dicarboxylic acid anhydride (41.5 g), 2-hydroxyethyl methacrylate (32.5 g), tetramethylammonium chloride (0.22 g), and 2,6-di-tert.butyl-4-methylphenol (0.15 g) was heated to 90° C. and stirred at that temperature for 10 hours to give the above-mentioned half-ester (60 g).

N-(2-Methacryloyloxy)ethyl)-2,3-dimethylmaleimide

This was prepared from N-(2-hydroxyethyl)-2,3-dimethylmaleimide and methacryloyl chloride analogously to the method described for the preparation of the 3-(methacryloyloxy)propyl homologue in Example 17 of British Patent Specification No. 1 544 840.

3-(Methacryloyloxy)-2-hydroxypropyl X,Y-dibromo-p-cresyl ether

To 250 g of commercially available X,Y-dibromo-p-cresyl glycidyl ether (epoxide content 2.76 equiv./kg., calculated value 3.11) were added 2,6-di-tert.butyl-p-cresol (0.5 g) and 1 g of tetramethylammonium chloride, and the solution was heated to 100° C. with stirring. Methacrylic acid (59.34 g) was added slowly over 1 hour at a rate such that the temperature of the mixture did not exceed 105° C. Heating at 100° C. was continued until the epoxide content had fallen to a negligibly low value. The product was a clear viscous liquid.

EXAMPLE 1

A composition comprising 10 parts of 3-(methacryloyloxy)-2-hydroxypropyl bicyclo [2.2.1]hept-2-ene-6-carboxylate and 1 part of benzil dimethyl ketal, which had a viscosity of about 0.25 Pa s, was applied by a spin coater as a layer approximately 20 μm thick onto copper plate. The coating was irradiated for 10 seconds with a medium pressure mercury lamp (80 w per cm) at a distance of 20 cm, and the coating became nontacky.

Next, the coating was irradiated through a negative at a distance of 25 cm from a medium pressure mercury lamp (30 w per cm) for 15 minutes, followed by development with cyclohexanone. A good relief image was obtained.

EXAMPLE 2

2-(Acryloyloxy)ethyl methyl-5-carboxybicyclo [2.2.1]hept-2-ene-6-carboxylate containing 10% of benzil dimethyl ketal, in the form of a coating about 20 μm thick, was irradiated for 2 seconds as in the first stage of Example 1, becoming nontacky. Next, the coating was irradiated as in the second stage for 15 minutes, a visible image being formed.

EXAMPLE 3

A composition comprising 10 parts of 2-(acryloyloxy)ethyl 5-carboxy-7-oxabicyclo [2.2.1]hept-2-ene-6-carboxylate and 1 part of benzil dimethyl ketal was irradiated for 15 seconds as in the first stage of Example 1, becoming nontacky. Next, it was irradiated for 15 minutes through a negative with a medium pressure mercury lamp (80 w per cm), a visible image being formed.

EXAMPLE 4

A composition comprising 2-(acryloyloxy)ethyl methyl-5-carboxybicyclo [2.2.1]hept-2-ene-6-carboxylate (30 parts), 3-(methacryloyloxy)-2-hydroxypropyl X,Y-dibromo-p-cresyl ether (30 parts), N-(2-(methacryloyloxy)ethyl)-2,3-dimethylmaleimide (8 parts), benzil dimethyl ketal (8 parts), and 2-chlorothioxanthone (2 parts) was irradiated for 15 seconds as described in the first stage of Example 1. Next, the coating was irradiated as in the second stage of that Example through a negative for 15 minutes followed by development in 1 M sodium hydroxide solution. An excellent relief image was produced.

EXAMPLE 5

A mixture of 45 parts of 2-(methacryloyloxy)ethyl methyl-5-carboxybicyclo [2.2.1]hept-2-ene-6-carboxylate and 45 parts of 3-(methacryloyloxy)-2-hydroxypropyl methyl-5-carbomethoxybicyclo- [2.2.1]hept-2-ene-6-carboxylate, containing 8 parts of benzil dimethyl ketal and 2 parts of 2-chlorothioxanthone, in the form of a layer about 20 μm thick, was irradiated with a medium pressure mercury lamp (80 w per cm) at a distance of 20 cm, the layer becoming tack-free after 10 to 15 seconds. Next, the coating was irradiated through a negative at a distance of 25 cm from a medium pressure mercury lamp (30 w per cm) for 10 minutes, followed by development with 0.1 M aqueous sodium hydroxide solution. An image was produced.

EXAMPLE 6

In a mixture of 60 parts of N-(2-(methacryloyloxy)ethyl) methylbicyclo [2.2.1]hept-2-ene-5,6-dicarboximide and 30 parts of 2-(methacryloyloxy)ethyl methyl-5-carboxybicyclo [2.2.1]hept-2-ene-6-carboxylate were incorporated 4 parts of benzil dimethyl ketal and 4 parts of 2-chlorothioxanthone by adding them dissolved in a small amount of acetone and briefly warming to 50° C. to remove the solvent. The composition was applied as in Example 5 except that exposure to irradiation for only 3 seconds was required to render the layer tack-free. After further exposure for 30 minutes an excellent image was obtained by development with brushing using 1% aqueous sodium carbonate solution.

EXAMPLE 7

3-(Methacryloyloxy)-2-hydroxypropyl X,Y-dibromo-p-cresyl ether (66 parts) and 2-(methacryloyloxy)ethyl 5-carboxy-7-oxabicyclo [2.2.1]hept-2-ene-6-carboxylate (33 parts) were mixed and blended with benzil dimethyl ketal (4 parts) and 2-chlorothioxanthone (4 parts). The composition was applied as in Example 5 except that the exposure to irradiation for only 5 seconds was required to render the layer tack-free. After further exposure for 30 minutes a good image was obtained by development with brushing using 0.1% aqueous sodium carbonate solution.

EXAMPLE 8

2-(Methacryloyloxy)ethyl methyl-5-carboxybicyclo [2.2.1]hept-2-ene-6-carboxylate (90 parts) and 3-(methacryloyloxy)-2-hydroxypropyl methyl-5-carbomethoxybicyclo [2.2.1]hept-2-ene-6-carboxylate (90 parts) were combined and blended with benzil dimethyl ketal (16 parts) and 2-chlorothioxanthone (4 parts). This composition was applied as a layer about 20 μm thick onto copper plate and irradiated with a medium pressure mercury lamp (80 w per cm) at a distance of 20 cm, the layer becoming tack-free after 10 seconds.

The coated plate was then stored in the dark at ambient temperature for 14 days, after which the coating was irradiated through a negative at a distance of 25 cm from a medium pressure mercury lamp (30 w per cm) for 60 minutes. Development with 2% sodium carbonate gave a durable image.

COMPARATIVE EXAMPLE

For purposes of comparison only, a composition comprising 45 parts of methylbicyclo [2.2.1]hept-2-ene-5,6-dicarboxylic acid anhydride, 45 parts of methacrylic acid, 8 parts of benzil dimethyl ketal, and 2 parts of 2-chlorothioxanthone was exposed in the form of a film to irradiation from a medium pressure mercury lamp (80 w per cm). After prolonged irradiation (more than 30 seconds) this composition, containing groups of formula I and groups of formula II in separate molecules, had not become tack-free.

What is claimed is:

1. A process for production of an image which comprises
 (1) exposing to actinic radiation a layer, supported on a carrier, of a liquid composition containing a compound (A) having in the same molecule both at least one group of formula

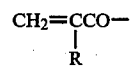  I and at least one group of formula

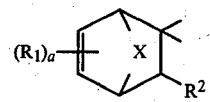  II such that the layer solidifies and becomes essentially nontacky due to photopolymerisation of (A) through the group or groups of formula I but remains substantially photocrosslinkable, and subsequently P1 (2) exposing as through an image-bearing transparency consisting of substantially opaque and substantially transparent areas at least part of the layer so solidified to a substantially greater amount of actinic radiation such that the further exposed part or parts of the photopolymerised layer undergo photocrosslinking through the group or groups of formula II, and
 (3) developing the image by dissolving in a solvent parts of the layer which have not become substantially photocrosslinked, where R denotes a hydrogen atom or a methyl group,
a is zero or an integer of from 1 to 4,
R₁ denotes a methyl group, or, if a is 1, may alternatively denote an allyl group,
R² denotes a hydrogen atom, a carboxyl group, a carbonyloxyalkyl group (which may be interrupted in the chain by an ether oxygen atom), a carbonyloxyalkene group joined through an oxygen atom to a group of formula I, the alkyl or alkylene group having up to 8 carbon atoms, or together with one of the indicated free valencies, R² denotes a cyclic imide group of structure

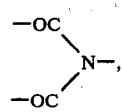

and

X denotes a methylene bridge, a methylene bridge substituted by one or two of the aforesaid methyl groups $R^1$, a methylene bridge substituted by the allyl group $R^1$, or an oxygen atom.

2. The process of claim 1 in which (A) is of formula

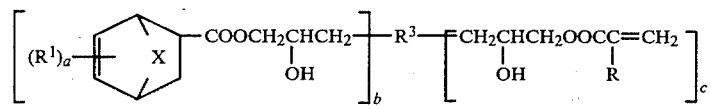  IV or

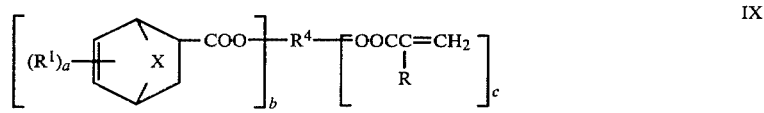  IX where
b and c are each independently an integer of at least 1,
$R^3$ denotes the residue of a compound containing at least (b+c) glycidyl groups directly attached to an atom or atoms of oxygen, nitrogen, or sulfur, after removal of (b+c) such glycidyl groups, and
$R^4$ denotes the residue, after removal of (b+c) alcoholic hydroxyl or phenolic hydroxyl groups respectively, of an alcohol having at least (b+c) alcoholic hydroxyl groups or of a phenol having at least (b+c) phenolic hydroxyl groups.

3. The process of claim 1 in which (A) is of formula

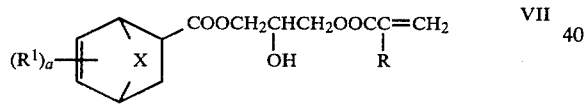  VII or

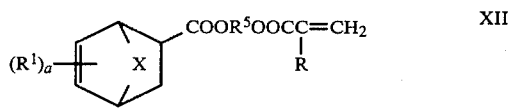  XII where $R^5$ denotes an alkylene group of 2 to 6 carbon atoms.

4. The process of claim 1 in which (A) is of formula

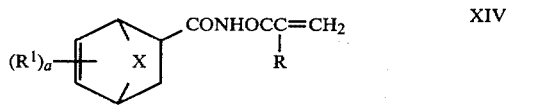  XIV or

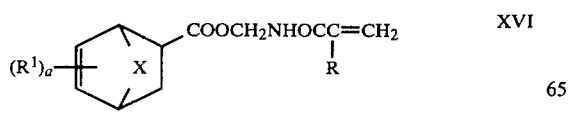  XVI or

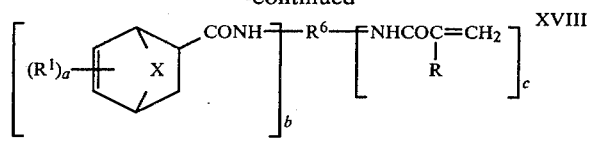  XVIII where
b and c are each independently an integer of at least 1 and
$R^6$ denotes the residue of a compound containing at least (b+c) primary amino groups, after removal of (b+c) such amino groups.

5. The process of claim 1 in which (A) is of formula

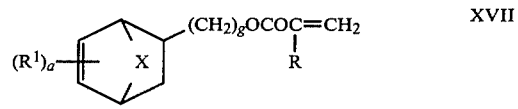  XVII or

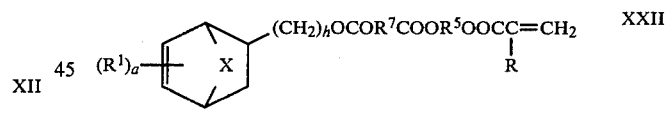  XXII or

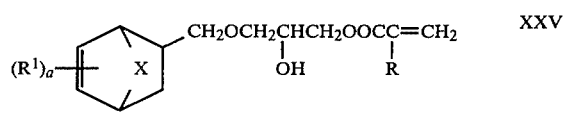  XXV or

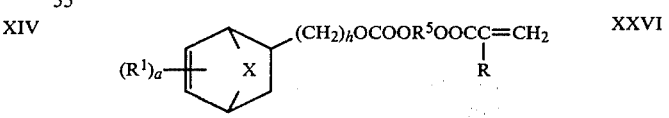  XXVI where
$R^5$ denotes an alkylene group of 2 to 6 carbon atoms,
$R^7$ denotes a carbon-carbon bond or a divalent group of 1 to 10 carbon atoms,
g denotes zero or 1, and
h denotes zero, 1, or 2.

6. The process of claim 1 in which (A) is of formula

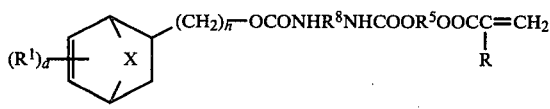

where
R⁵ denotes an alkylene group of 2 to 6 carbon atoms,
h denotes zero, 1, or 2, and
R⁸ represents the residue, after removal of the two isocyanate groups, of an organic di-isocyanate.

7. The process of claim 1 in which (A) is of formula

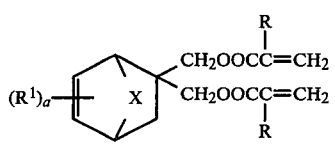

or

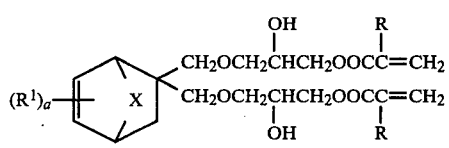

8. The process of claim 1 in which (A) is of formula

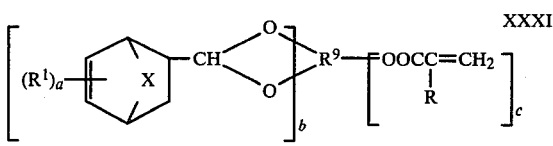

where
b and c are each independently an integer of at least 1 and
R⁹ denotes the residue of a compound containing at least (2b+c) alcoholic hydroxyl groups, after removal of (2b+c) alcoholic hydroxyl groups.

9. The process of claim 1 in which (A) is of formula

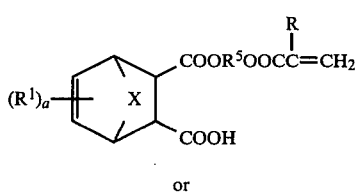

or

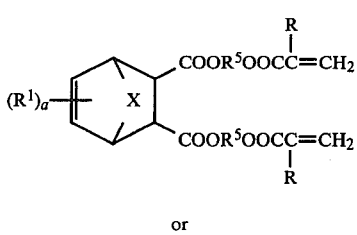

or

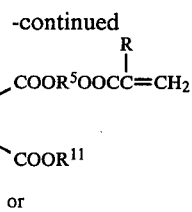

or

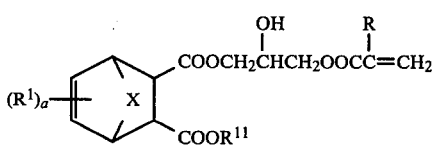

where
R⁵ denotes an alkylene group of 2 to 6 carbon atoms and
R¹¹ denotes an alkyl group of 1 to 8 carbon atoms, or an alkyl group of 1 to 8 carbon atoms interrupted in the chain by an ether oxygen atom.

10. The process of claim 1 in which (A) is of formula

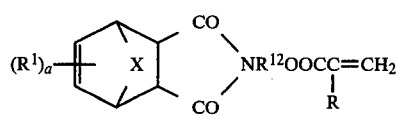

where R¹² denotes as alkylene group of 1 to 6 carbon atoms.

11. The process of claim 1 in which (A) is 3-(methacryloyloxy)-2-hydroxypropyl bicyclo[2.2.1]hept-2-ene-6-carboxylate, 2-(acryloyloxy)ethyl methyl-5-carboxybicyclo[2.2.1]hept-2-ene-6-carboxylate, 2-(acryloyloxy)ethyl 5-carboxy-7-oxabicyclo[2.2.1]hept-2-ene-6-carboxylate, 2-(methacryloyloxy)ethyl methyl-5-carboxybicyclo[2.2.1]hept-2-ene-6-carboxylate, 3-(methacryloyloxy)-2-hydroxypropyl methyl-5-carbomethoxybicyclo[2.2.1]hept-2-ene-6-carboxylate, 2-(methacryloyloxy)ethyl 5-carboxy-7-oxabicyclo[2.2.1]hept-2-ene-6-carboxylate, or N-2-(methacryloyloxy)ethyl methylbicyclo[2.2.1]hept-2-ene-5,6-dicarboximide.

12. The process of claim 1 in which the said liquid composition contains as (A) a compound of formula

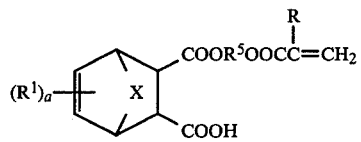

where R⁵ denotes an alkylene group of 2 to 6 carbon atoms
and further contains a compound (B) which has in the molecule both at least one group of formula I and at least one free sulfonic, phosphonic, or carboxylic acid group but has no group of formula II, and the solvent employed for development of the image is an aqueous solution of a base.

13. The process of claim 1 in which the said liquid composition also contains a compound (B) which has in the molecule both at least one group of formula I and at least one primary, secondary, or tertiary amino group but has no group of formula II, and the solvent employed for development of the image is an aqueous solution of an acid.

* * * * *